United States Patent [19]

Eastman

[11] 4,030,486
[45] June 21, 1977

[54] APPARATUS FOR MEASURING DEFLECTION AND TEMPORAL VALUES ON ELECTROCARDIAC TRACINGS

[76] Inventor: George Eastman, 102 Old Clairton Road, Pittsburgh, Pa.

[22] Filed: May 15, 1975

[21] Appl. No.: 577,873

Related U.S. Application Data

[62] Division of Ser. No. 831,954, June 10, 1969, Pat. No. 3,884,221.

[52] U.S. Cl. .......................... 128/2.06 R; 33/1 C; 33/107 R; 235/70 B
[51] Int. Cl.² ......................................... A61B 5/04
[58] Field of Search ............... 128/2.05 Q, 2.05 R, 128/2.06 G, 2.06 R; 235/69, 70 A, 70 B, 70 R, 124; 33/1 C, 1 M, 107 R, 111, 174 J, 177, 189, 340

[56] References Cited

UNITED STATES PATENTS

| | | | |
|---|---|---|---|
| 1,560,599 | 11/1925 | Moler | 235/70 B |
| 2,088,533 | 7/1937 | Phelps | 33/1 C |
| 2,501,550 | 3/1950 | Tamagna et al. | 33/1 C |
| 2,736,097 | 2/1956 | Coleman, Jr. | 235/70 B |
| 3,346,960 | 10/1967 | Miles | 33/1 M |

FOREIGN PATENTS OR APPLICATIONS 170,732  11/1921  United Kingdom .............. 33/1 C

*Primary Examiner*—William E. Kamm
*Attorney, Agent, or Firm*—Lawrence G. Zurawsky

[57] ABSTRACT

This disclosure relates to a method and specific apparatus for extracting significant data values, analogous temporally and electrically to the physiologic myocardial action potential which accompanies each cardiac contraction, from conventionally recorded electrocardiograms. The apparatus for measuring deflection and temporal values from said conventional electrocardiograms is comprises of three transparent elements. One of the elements constructed to be positioned over the electrocardiogram to be measured and has integral therewith a grid, while the two remaining elements are slideably positioned one over the other on the said positioned element such that their movement is at right angles to each other.

3 Claims, 5 Drawing Figures

| | P | Q | R | S | R' | S' | R" | J | T |
|---|---|---|---|---|---|---|---|---|---|
| I | | | | | | | | | |
| aV_f | | | | | | | | | |
| V_1 or V_2 | | | | | | | | | |

| TIME VALUES | COMPLEX | | | | | |
|---|---|---|---|---|---|---|
| | 1 | 2 | 3 | 4 | 5 | 6 |
| $P_i$ | | | | | | |
| $P_t$ | | | | | | |
| $Q_i$ or $R_i$ | | | | | | |
| $R_t$ or $S_t$, etc. | | | | | | |
| $T_i$ | | | | | | |
| $T_t$ | | | | | | |
Fig. 3
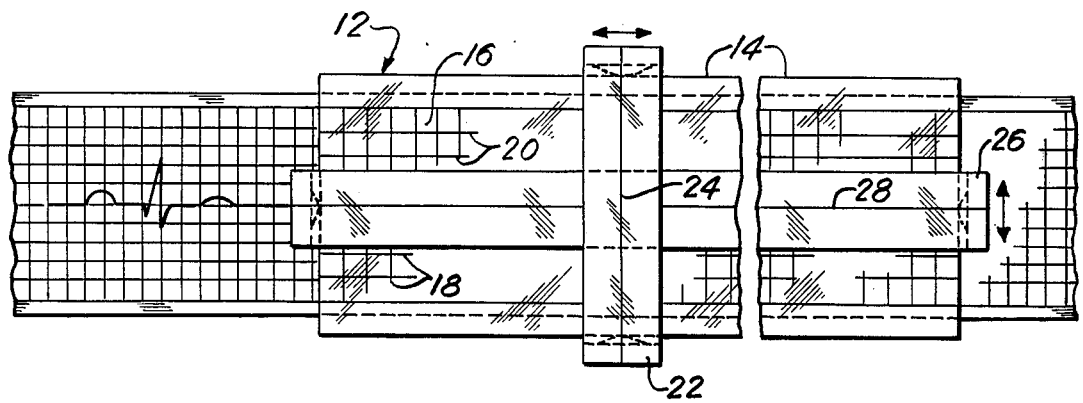
Fig. 4
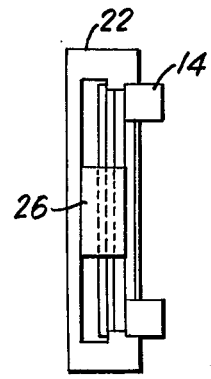
Fig. 4a

APPARATUS FOR MEASURING DEFLECTION AND TEMPORAL VALUES ON ELECTROCARDIAC TRACINGS

This application is a division of Patent No. 3,884,221 issued May 20, 1975 having Ser. No. 831,954, filed June 10, 1969.

This invention relates to a method, apparatus and programs for the interpretation of, and physiologic and clinical diagnosis of the clinical electrocardiogram, hereinafter referred to for brevity as the "ECG".

Heretofore, two methods, one commonly used and one of major research interest (but of limited widespread clinical usefulness) have been employed. Those are (a) interpretation of human observation, memory recall and analysis of the individual tracing set (the ECG) by specially trained and experienced physicians known as electrocardiographers, and (b) employment of more or less complete logic pathways and diagrams for classification, of numerical data derived from electrocardiographic leads of their electrical analogue voltages, by a digital computer into diagnostic categories of clinical interest. Those two categories of interpretation will hereinafter be referred to as human and computer diagnostic methods, respectively. All human methods and some computer methods begin with the recording of scalar cardiac action potential derivative voltages from electrodes temporarily fastened to the patient's upper and lower extremities and subsequently to selected point areas across the anterior of the patient's thoracic cage. From these are recorded twelve linear tracings which measure body-surface-point to common ground, or point-to-point instantaneous current flow values. Those values are interpreted, by virtue of their interaction with a high, fixed and internal-to-machine impedance, as potential differences and are so recorded. Those potentials are of the order of 10 microvolts, minimal readable deflections, to a maximum of 10 millivolts, maximum machine obtainable deflection magnitude. The tracings so obtained are by convention called leads and are labelled I, II, III, $aV_r$, $aV_1$, $aV_f$, and $V_1$, $V_2$, $V_3$, $V_4$, $V_5$, and $V_6$. Those twelve leads are by convention, in the absence of interfering skeletal muscle action potentials, assumed to represent projections of the underlying myocardial action potential on the body surface. The ultimate generating source for the observed potentials is the muscle of the heart chambers in the process of orderly and regular intermittent contraction, to wit the right and left atria and the right and left ventricles. The myocardial potential is, in fact, the sum of the electrical forces released from the various portions of the myocardium to the surface of the body as each cell thereof undergoes successive depolarization and repolarization.

The summated effect of the electrical force generated by each cell is held to be equivalent to that which would be generated by a single electrical dipole of continuously variable magnitude from zero to a given maximum and of continuously variable three dimensional positions throughout any combination of the available 360° of azimuth and 360° of elevation on the surface of a conventional sphere of spherical trigonometry having its center located at the center of the conventional xyz, Cartesian, three-dimensional, coordinate system and having its three right angle crossed diameters coincident with those axes.

Each lead is represented as summing the effects of the electrical forces generated within a right circular conicoid figure of arbitrary apex angle, with the apex located at a given spherical surface point, with the major axis of the conicoid figure coincident with the spherical diameter projected through that point and with the base of the conicoid figure being the swept-out, opposite spherical surface. In that system, the surface potential difference, $V_s$, inversely can be assured to vary directly as a function of $V_i$ and inversely as a function of the square of $d$ where $V_i$ is the internal potential difference of the generating potential difference and $d$ is the difference measured from the hypothetical generating dipole to the recording electrode.

Each lead tracing consists of the recorded potential difference on its vertical axis, and lapsed time on its horizontal axis, of a successive series of cardiac contractions. Examination of the order, or lack thereof, and the regularity in time, or lack thereof, of the succession of a series of deflections within one or more leads up to a total of the twelve available leads enables the reading electrocardiographer of observation and measurement to determine whether the entire heart and/or component portions are contracting in a normal, expected and orderly fashion or to determine the contrary.

Detection of an irregularity or a series of irregularities then leads to comparison of their characteristics with the characteristics previously observed in other tracings by this particular observer, or recorded in the literature of the field, or both, thus permitting in nearly every instance the classification of the type or rhythm disturbance (hereinafter referred to as "arrhythmia") into defnite nosological and/or clinical diagnostic categories. Examination of a combination of specific temporal interrelationships and associated voltage values of given parts of the deflections enables the electrocardiographer to determine the normality or abnormality of impulse conduction throughout the successively depolarized and repolarized portions of the myocardium; and to make similar deductions to those described under arrythmias above, but in this portion of his analysis, to apply criteria for the classification of the nature, location, type and severity of the observed conduction defect.

Examination and measurement of voltage values, particularly, and temporal values to a much lesser extent than in the arrhythmia and conduction defect sections described above, enables the electrocardiographer to make deductions about the functional status and/or integrity of the heart muscle. This portion of the diagnostic procedure will hereinafter be referred to as the "myocardial", or "heart muscle", or "muscle" diagnosis.

In the heart muscle diagnosis portion, one can detect discreet random defects as in myocardial infractions; specific chamber dilatation, hypertrophy and/or malfunction as in valvular heart disease, congenital or acquired, and also as in early hypertensive heart disease; and/or generalized muscle hypertrophy fibrosis and/or dilatation as in late hypertensive heart disease, active rheumatic heart disease and the various cardiomyopathies. The above list of etiologies of mycardial disease detectable by electrocardiography is a representative listing of the commonly diagnosed lesions, but does not exclude from ECG diagnoses various other rarer lesions.

The widely practiced human interpretations of electrocardiograms can be seen as both a science and as an art and at least a portion of its inductive and deductive reasoning is carried out by intuitive or heuristic methods which do not permit totally accurate evaluation and/or individual performance comparisons.

Even though the actual myocardial event is a three dimensional one with continuously variable vectors having both magnitude and free spherical surface movement available, instrumentation has reduced the data supplied to the human ECG interpretor to a series of scaler (one dimensional) tracings of variable scanning directions and variable surface representation of underlying changing voltage events. In an imperfect and relatively naive sense, it is possible for the ECG interpreter to catch a dim view of what must have been the actually occurring three dimensional event, but given the complexity of the question involved and the consequent requirement for numerical data processing, it is beyond the capability of human mind to analyze, characterize, and process the material necessary. In essence, the need is for an apparatus and method to run back up the scale of complexity from one dimensional to two dimensional and finally to three dimensional spatial reasoning; that same scale down which the data was degraded for necessary instrumental reasons in the recording of the electrocardiogram.

Human electrocardiographers rely for their interpretation only minimally on vectorcardiographic reasoning (and that amount as seen above only in an inaccurate and imperfect way). Instead, their principal methodology is by comparisons, lead by lead, portions of one lead as compared to similar portions of other leads, and different portions of the same lead all intercompared. This technic is known as pattern reading and will be so described hereinafter. It relies on mental and possibly physical storage of previous ECGs recorded from other patients, and mental or physical retrieval of the significant portions of those tracings for comparison purposes.

The necessity for long training and experience for carrying out human interpretation is obvious. Other factors limiting the accuracy of human interpretation include the day to day variability of the performance of the individuals doing this task, the necessity to screen superfluous input data for contradictory and/or illogical information, and the necessity to accord due and proper weight to the manifestations of several concurrently present disease processes observed in a single tracing.

The above mentioned limitations, coupled with the non-availability of electrocardiographers in many small community hospitals, has led to a number of projects published in the medical literature attempting to so handle data initially generated by the myocardial action potential and variously recorded that this data could be processed and "diagnosed" by digital computer methodology.

SUMMARY OF THE INVENTION

According to this invention a conventional ECG tracing is obtained from either the immediate recording from a patient using any standard electrocardiograph or it may be obtained by later reference to a tracing similarly recorded (and filed) at any past time.

The tracing is measured by using the apparatus of the invention, recording values along the horizontal (time) axis for a succession of deflections contained in lead I and along the vertical (voltage) axis using deflections found in leads I, $aV_f$ and V, or $V_2$.

In the first case, the points measured include the initiation and termination of the constituent major deflection entities, i.e. the P wave, the QRS complex, the T wave and rarely any successor waves. In the second case there is measured the instantaneous voltage maxima attained (either positive or negative) for each of the deflection entities, i.e. the P, Q, R, S, R', S', R" and J and T, with the absence of any one recorded as a null (zero) value.

This data is then entered by standard point input technics into a digital computer which first verifies by comparision the sign correctness and "physiologic possibility" of the input data.

Then by use of a master program directing the sequential data manipulation according to the method of this invention, the time and voltage parameters of the three dimensional electrical phenomena which ab initio generated the electrocardiogram under examination are approximated.

Part of the stored program comprises a body of previously calculated three dimensional data points and temporal points obtained from numerous normal ECGs for cardiac tracings exhibiting no physiological abnormalities. In addition to the stored comparative data for normal ECG tracings, the program provides comparative data for each type of cardiac abnormality that might be encountered and a statistical comparision of the three dimensional and temporal data for each type of cardiac abnormality with similar data exhibited by the normal ECG. According to the method of this invention, the spatial vector and temporal data for the ECG to be analyzed are compared with the stored data for the normal ECGs and for abnormal ECGs to determine the likelihood of existence of a cardiac abnormality, what the nature of the probable abnormality is, and the statistical probability of the existence of each type of abnormality considered.

After comparison and diagnosis of the ECG data, the program is adapted to supply directly to the sender, an output indicating the probability of normality of the submitted electrocardiogram and the concommitant probability of the existence of any specific cardiac abnormality.

The apparatus of this invention used in conjunction with the method described, provides a reliable, rapid and inexpensive means for obtaining interpretation and diagnosis of ECGs which permits the wide spread use, by virtually all hospitals and medical practitioners, wherever geographically situated, of computerized interpretation of ECGs and diagnoses therefrom. The method and apparatus employed reduce substantially the amount of data needed for interpretation and diagnosis of ECGs and provide reliable and consistent means of analysing ECGs which circumvent the possibility of variation and error inherent in human interpretation of such data.

It is an object of this invention to provide a voltage deflection and temporal measuring apparatus for use with a method for interpretation of ECGs based upon substantially less basic data from the ECG tracing than was heretofore required.

Other objects and advantages of the present invention will become apparent from the ensueing description, in the course of which, reference is had to the accompanying drawings in which:

FIG. 3 is an illustration of the data form containing input data for analysis of the temporal parameters contained in the ECG under study.

FIG. 4 shows the apparatus employed in reading the data required for the method of this invention from the ECG tracing.

FIG. 4A is a side view of FIG. 4.

Figures 1, 2:
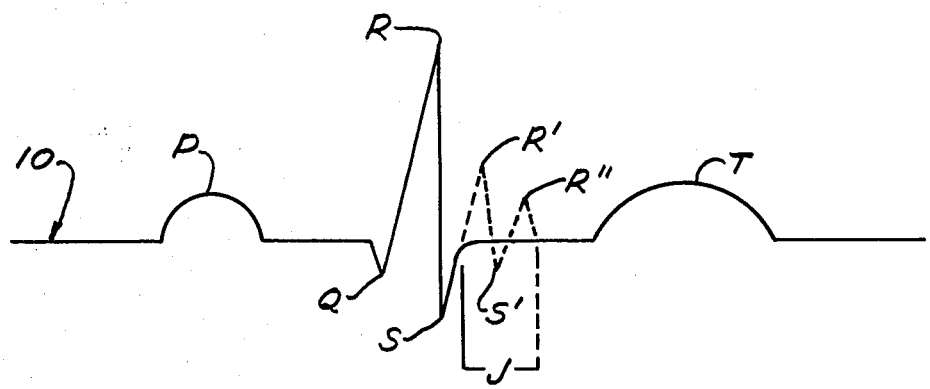
FIG. 1 is a composite illustration of the various ECG wave forms that might appear in the conventional tracing.
FIG. 2 is an illustration of the data form employed in recording the data from FIG. 1 and serves as a starting point for the data processing described in the method described below.

A description of the above will follow and then the novel features of the invention will be presented in the appended claims.

At the outset, a conventional ECG tracing is obtained using any of the available clinical electrocardiographs, recorded at the normal speed of 50 millimeters per second and standardized at the normal value of 10 millimeters deflection equivalent to the standard reference 1 millivolt voltage.

Either from the ECG in its unmounted or strip form, or after mounting of the various lead tracings, on any one of the available standard mounting cards, or on a copy of a so-mounted ECG made from the original by any of the standard photocopy processes, values are then measured. The measuring instrument of FIG. 4 and 4A constitutes the apparatus of this invention and it measures, using the vertical and horizontal cursors as appropriate, voltage deflection values, and time values. The voltage deflection values are measured along the vertical axis and the time values along the horizontal axis.

The rhythm and conduction diagnosis portion of the procedure are obtained from lead I solely and a succession of a minimum of six and a maximum of fifteen deflections are measured with reference to the initiation and termination of the normally found P waves, the time values of the initiation and completion of the set of deflections comprising the QRS complex and the initiation and completion of the T wave.

In the muscle diagnostic portion of the program representative single deflections are measured in three leads, namely lead I, lead $aV_f$, and either lead $V_1$ or $V_2$. Those measurements are made using the vertical scale and in essence constitute measurement of the maximum departure from the base line, either in an upward or downward direction, of the following constituents of each complex considered: the P wave; the constituent parts of the QRS deflection; namely, the Q wave, the R wave, the S wave, the J or QRST segment junction; and also, if present, the additional waves labeled R', the S' and the R'', and finally the height of the concluding wave of the complex, the T wave.

These measurements, insofar as the technician performing the procedure is concerned, are made in millimeter blocks and are coupled with a visual estimation using the magnification built into the scale for the estimation of additional amounts in tenths of a millimeter. Insofar as the technician is concerned, he or she is simply measuring amounts in blocks and tenths of blocks. In actual fact, by reason of the standardization of the ECG on the horizontal or time schedule as noted above, the measurement is translatable into fractional seconds by the fixed relationship that, on the horizontal scale, one millimeter is equal to 0.02 seconds or 20 milliseconds while the vertical scale is so standardized that one millimeter is equal to 1/10 millivolt or 100 microvolts. The data obtained in seconds or milliseconds and millivolts or microvolts is entered by the reading technician into a form containing two data tables as disclosed herein and is then transmitted to a centrally located computer which proceeds through the following steps:

a. In accordance with the process and program herein disclosed, the time values are scanned and the degree of regularity or irregularity of the sequency of similar portions of each deflection and different portions within the same deflection are compared to standards prerecorded in the computer memory bank and by means of such comparisons a decision is reached as to whether the succession of tracings occur regularly, regularly irregular or irregularly irregular. If either of the two later circumstances is obtained, the type of irregularity is further compared with previous stored standards and a decision is reached as to which of a variety of print out diagnoses will eventually be supplied for the interpretation of this particular tracing at the completion of the remaining portion of the program.

b. The vertically inscribed data for representation complexes as described above is subjected to a process of appropriate combinations, extractions and recombinations of data of the several variables presented as input to determine the magnitude and phase angles of each of a series of selected two dimensional or planar vectors representative of the motion of the cardiac action current in a particular plane. Then two orthogonal planar vector series are further combined to yield a set of successive vectors of from 8 to 10 members of each series, which in numerical form, or in the form of a three dimensional wire or rod model, can express a reasonable clinical approximation to the magnitude and direction of the underlying generating dipole myocardial action current.

It should be emphasized that the process of determining the vector representations of the myocardial action current from the particular available data base is unique to this method. It requires the voltage deflection and temporal value measuring apparatus herein described to obtain the necessary reading accuracy of the tracings concerned and, having as it does a starting point of a commonly produced and commonly generated tracing, it has far wider applicability than any available or conventional methods.

Additionally, from the succession of vectors described in the paragraphs above, the method and apparatus herein disclosed provide for the determination of discriminate vector values which do not directly exist in electrically analogue form in the myocardial current but which nevertheless have significant diagnostic capabilities. Those values include approximations of quantities referred to herein as the ventricular grandient, three Eigenvectors referred to herein as Eigenvectors A, B, and C, and the polar vector.

Even granting a capability on the part of a human electrocardiographer to appreciate, but not quantitate, the existence and approximate direction of the constituent vector succession of the myocardial action current, the secondarily derived vector magnitudes are completely beyond any unaided human capability of such comprehensive accurate and reliable reconstruction on observation of the original tracing and require the use of this invention's measurement device and the process of vector construction followed by appropriate vector combinations for their successful achievement.

c. Finally attention is directed to specific circumstances in which prolongation of the time interval between the onset of the P wave and the onset of the QRS complex, or between the onset and termination of the QRS complex, or either prolongation or undue shortening exists in the time span between the beginning of the QRS complex and the ending of the T wave.

If an observation of prolongation or shortening of any of those time intervals is observed, a tentative diagnosis of the existence of a conduction defect can be made. Reference is then required to the original time measurement program specified under (a) above and the "myocardial program" described under (b) for the determination of the nature of the conduction defect and its location.

Generally prolongation of the time interval between the onset of the P wave and the beginning of the QRS complex can be assumed to represent delay in transmission of the cardiac impulse from the atria to the ventricles and its quantitation yields a finding of first or second degree of A-V block and further investigation is required as to whether the degree of prolongation is fixed or variable for the separation out of the Wenkebach phenomenon. In the event that the degree of the A-V block exceeds a given value, a diagnosis of third degree block is made and then reference is had to the vector characteristics of the QRS complex as determined in the method described in (b) above for the determination of the site of onset and excitation of the ventricular complexes observed.

The shortening of the interval from the beginning of the P wave to the beginning of the QRS wave is read by the time detection portion of the program as representative of the Wolf-Parkinson-White syndrome and, as such, again requires reference to the myocardial portion of the program to determine whether there is present or absent a classic delta pattern also diagnostic of this syndrome.

In the matter of prolongation of the QRS interval, a diagnosis of bundle branch block is tentatively entertained and reference to the myocardiom program ascertains whether vector loop changes characteristic of either right of left disease of the bundle branch exists. Similarly, a finding of a successive vector loop pattern suggestive of bundle branch block during the myocardial portion of the program leads to reference to the time portion to determine whether prolongation of the QRS interval exists and, when both are found to coexist, an appropriate diagnosis of conduction defect is made.

In the arrhythmia diagnostic section labeled (a) above, the finding of a regular irregularity produces additional instructions to the person entering data, requesting entry of the QRS parameters of the cardiac contraction occurring with regular irregularity and at a time interval earlier than one might anticipate its occurrence in a regular sequence. This contraction is compared with those of the right and left bundle branch block types and, because of clinical circumstances, is labeled not as right and left bundle branch blocks, but as ventricular premature beats occurring with an exciting focus in either the right or left ventricle, respectively.

Alterations in either direction of the time interval from the beginning of the QRS complex to the completion of the T wave are interpreted along with derived information concerning the T vector as determined in the basic myocardial program (b) above. In this portion of the program, comparison of the characteristics of the T wave with the prolongations or shortening of the interval enables diagnoses to be made of abnormalities in electrolyte concentration in the myocardial extra and intracellular fluids.

When the above programs (a), (b) and (c) are completed, information in numerical form generated by each of the programs successively, and by the interactions between them as described in the paragraphs immediately above, is stored and retained in a temporary computer memory bank. Stored in a permanent computer memory bank are the mean values and standard deviations for all of the temporal event measurements, and for the magnitudes and phase angles of the planar vectors and for the magnitudes, azimuths and elevations of the three dimensional vectors and also for the constructed vector quantities; namely, the ventricular gradients and the Eigenvectors. Those mean values are all accompanied by appropriate standard deviations about those means as determined by prior programming into the machine of a large series of both normal and abnormal tracings with appropriate labels so that the nature of each mean standard deviation can be adequately, accurately and promptly established.

The next immediate step in data processing is the direction to the machine to compare each of the series of temporal values and constructed vector values with the normal anticipated values. Then an approximation is made of the difference in terms of standard deviations and fractions thereof from the anticipated normal means. The standard deviation difference pattern is retained in another section of temporary memory storage and a similar standard deviation difference pattern is established for each of the considered pre-programmed diagnoses.

Those diagnoses in which the standard deviation difference values are appropriately summed with weighting factors applied to the vectors of greatest discriminate value, are then successively considered as possible diagnoses for an unlimited number of unknown tracings. Any and all tracings which yield a probability value in excess of a p of 0.05 are then subjected to multi-variant regression analysis with differences calculated between the observed temporal and vector values of greatest discriminate capability.

The result of the multi-variant analysis is a probability score expressible in percentage terms of the concordance of the unknown input tracing with the previous established pattern of tracing characteristics as found in the computer's memory storage. This is sent back from the computer to the user in the form of an alphabetic-decimal print-out giving the major diagnoses listed in order of probability and their attached probability estimates. The print-out concludes with the statement that all other diagnoses considered have probabilities of less than 5.0 percent.

The method and apparatus employed for constructing a three dimensional model of the cardiac cycle from the one dimensional data of a conventional ECG tracing are explained in detail below with reference to the accompanying drawings. FIG. 1 depicts a conventional ECG tracing indicated generally by reference numeral 10. The deflections are represented by the upper case letters P through T in accordance with accepted medical convention. The phantom lines representing deflections R', S' and R" indicate those deflections which might be absent from certain tracings and the junction point, J, is shown as the junction between the end of the QRS segment and the beginning of the T segment.

According to the method and apparatus employed, an ECG is obtained from the patient using the conventional number of twelve leads. In most circumstances in which the method of this invention is used, the data from the twelve leads conventionally employed is not required; therefore, in a preferred embodiment of this invention, the data required will be only that obtainable from the leads I, $aV$ and either $V_1$ or $V_2$. In certain special cases involving complicated diagnoses, additional data might be required from the tracings obtained from other leads; however, the great majority of cardiac abnormalities can be diagnosed from the three tracings specified above.

One advantage of the method and apparatus employed is found in the fact that the necessary data can be obtained from the ECG tracings by a clerk or technician who need not be skilled in the medical arts or in the interpretation of ECGs. Using the data reader of this invention depicted in FIG. 4, and FIG. 4A which is explained more fully below, the clerk is able to fill in rapidly the data form depicted in FIG. 2 for each of the leads I, $aV_f$, and either $V_1$ or $V_2$.

Inspection of FIGS. 1 and 2 will shown that the data recorded comprises the voltage reading for each of the deflection points P, Q, R, S and T. In FIG. 1, the deflection points R', R'' and S' are indicated by phantom lines because those points, or any one of them, might not be present in a particular ECG tracing. In those circumstances, where R' R'' or S' is absent from the tracing, a zero is recorded in the relevant data block on the table of FIG. 2.

The data recorded in FIG. 2 corresponds to that representing the series of differing peak voltage values attained during one complete cardiac cycle beginning with the inception of the P wave and continuing through to the end of the T wave. As can be seen from inspection of FIG. 3, initiation and termination data points are determined from a plurality of complete cardiac cycles for one lead only and are used in the determination of the cardiac rhythym and conduction properties. The data compiled in FIGS. 2 and 3 is thereafter processed by a program which is set forth in detail in my U.S. Pat. No.3,884,221. It is possible, using the method and program of my U.S. Pat. No. 3,884,221 to construct a wire model three dimensional vector loop, a rectangular parallelapiped structure enclosing that vector loop, having its three sides terminating in a single three dimensional right angle relationship, the three Eigenvectors A, B, and C and to construct a solid body having its origin at the center of a sphere extending to the surface of one sphere in the case of the M vector and extending to the surface of still another larger or smaller sphere in the case of the T vector with a determination of the straight line or curvilinear line connecting the two located data points on the surface of the two spheres and a solid angle between.

It is also possible to use these models in visual comparison with a set of models representative of the normal ECG and representative of the ECG in various clinical states of abnormal myocardial function. Such a visual comparison would be an aid to the diagnosis. It would be possible to measure the differences between the models derived from any input ECG and a succession of models as described above. From this, one might derive a pattern of the degree of similarity or dissimilarity between the calculated model and the models of the already diagnosed disease conditions.

The third and principal area of usefullness is to describe the essential construction parameters for such a model without resorting to the actual construction and then to compare, by a multi-variant regression analysis, all of the input features with all of the features of the normal electrocardiogram as calculated similarly over a large series with appended standard deviations of each value and also all of the parameters of the multiplicity of clinical diagnoses. In this fashion, entirely analogous to the model as described above, it is possible to arrive at an estimate of the probability of any one input tracing resembling any one or more of the prototype tracing characteristics stored in the machine's memory. It is in fact a more accurate and probably diagnostically more meaningful procedure to function in this manner than the making of the mechanical model but both processes are entirely analogous and both represent innovations in the art, being possible from a normal electrocardiographic tracing only and for the first time by this method.

The apparatus of this invention comprises the measuring apparatus illustrated in FIG. 4 and indicated generally by reference numeral 12. The apparatus comprises a reading element 14 having integral therewith a grid 16 consisting of a set of parallel time lines 18 and a set of parallel voltage lines 20 perpendicular to the time lines. Adjacent time lines 18 are spaced one millimeter apart providing a unit of 20.0 milliseconds between adjacent time lines. Adjacent voltage lines are spaced one millimeter apart providing a unit of 100.0 microvolts between adjacent voltage lines. Reading element 14 is constructed of any transparent material and preferably is constructed to magnify the segment of the tracing being read.

A time cursor 22, slidably engaging and detachable from two opposite sides of reading element 14, has a hairline 24 constructed and arranged to delineate clearly the value and exact point being measured on the time scale. A voltage cursor 26, slidably engaging and detachable from the other two opposing sides of reading element 14, has a hairline 28 constructed and arranged to delineate clearly the value and exact point being measured on a specific voltage deflection.

The measuring apparatus of this invention is particularly adapted for use with the method described by the specific grid construction which is interrelated with the scales of time and voltage printed on the conventional electrocardiogram. In addition, no specific units appear on the reading element 14 or either cursor 22 or cursor 26. Therefore, no particular skill or experience is necessary for the clerk or operator recording the ECG data except for the counting and recording of blocks and tenths of blocks with the aid of a cursor. The requisite units of measurement and conversion can be previously stored in the computer or other means employed to effect the construction of the ultimate vector models.

The apparatus of the invention and the method described provide a reliable, rapid and inexpensive means for obtaining interpretations and diagnoses of ECGs which permit widespread use by virtually all hospitals and practitioners, wherever geographically situated, of computerized interpretation of ECGs and diagnoses therefrom. The method of this invention reduces substantially the amount of input data needed for the computer interpretation and diagnosis of ECGs and provides a reliable and consistent means of analyzing ECGs which obviate the possibility of variation and error in the human interpretation of such data.

According to the provisions of the patent statutes, the principle, preferred construction and mode of operation of the invention have been explained and what are considered the best embodiments have been illustrated and described. However, it should be understood that within the scope of the appended claims, the invention may be practiced otherwise than as specifically illustrated and described.

I claim:

1. Apparatus for measuring voltage deflection values and temporal values on electrocardiographic tracings comprising, transparent reading means having a grid integral therewith constructed and arranged to divide the tracing into discrete units of voltages and time, first cursor means slidably engaging two opposing sides of said reading means and detachable therefrom and constructed and arranged to delineate a discrete time value on the tracing, and second cursor means slidably engaging two other opposing sides of said reading means and detachable therefrom and constructed and arranged to delineate a discrete voltage value on the tracing.

2. Apparatus as described in claim 1 wherein said reading means is constructed and arranged to magnify the portion of the tracing being measured.

3. Apparatus as described in claim 1 wherein said grid comprises a set of parallel time lines spaced one millimeter apart to provide a unit of 20.0 milliseconds between adjacent time lines and a set of parallel voltage lines perpendicular to the time lines and spaced one millimeter apart to provide a unit of 100.0 microvolts between adjacent voltage line.

* * * * *